United States Patent [19]

Gelfand

[11] 4,010,214
[45] Mar. 1, 1977

[54] PROCESS FOR THE PREPARATION OF 2,5-DICHLORO-P-XYLENE

[75] Inventor: Samuel Gelfand, Lewiston, N.Y.

[73] Assignee: Hooker Chemicals & Plastics Corporation, Niagara Falls, N.Y.

[22] Filed: Feb. 4, 1975

[21] Appl. No.: 547,067

[52] U.S. Cl. .................. 260/650 R; 252/429 A
[51] Int. Cl.² ...................................... C07C 25/02
[58] Field of Search ............................. 260/650 R

[56] References Cited

UNITED STATES PATENTS

| | | | |
|---|---|---|---|
| 1,741,305 | 12/1929 | Jaeger | 260/650 R |
| 3,035,103 | 5/1962 | Hlynsky | 260/650 R |
| 3,226,447 | 12/1965 | Bing et al. | 260/650 R |
| 3,692,850 | 9/1972 | DiBella | 260/650 R |

*Primary Examiner*—D. Horwitz
*Attorney, Agent, or Firm*—Peter F. Casella; William J. Crossetta, Jr.; Arthur S. Cookfair

[57] ABSTRACT

A process for the preparation of 2,5-dichloro-p-xylene comprises reacting p-xylene with chlorine in the presence of a catalyst system comprising a catalyst selected from the group consisting of halides of iron, halides of antimony and mixtures thereof and a co-catalyst selected from the group consisting of organic sulfur compounds characterized by the presence of divalent sulfur.

7 Claims, No Drawings

PROCESS FOR THE PREPARATION OF 2,5-DICHLORO-P-XYLENE

BACKGROUND OF THE INVENTION

It is known that p-xylene can be reacted with chlorine in the presence of a catalyst to produce a mixture of various ring-chlorinated compounds and isomers including 2,5-dichloro-p-xylene, a compound useful as an intermediate in the preparation of pesticides and polymeric materials. Such reactions may be effected in solution, in suspension or in the absence of a solvent. Thus, for example, in U.S. Pat. No. 2,412,389, it is disclosed that p-xylene may be chlorinated in the presence of a catalyst such as iron filings or ferric chloride, to produce mixtures of nuclear chlorinated materials which may then be separated by a series of steps to isolate some components of the mixture. However, the various compounds and isomers which may be produced in this manner are not of equal commercial importance or value. Although such a procedure may be of value in the production of mixtures of variously ring-chlorinated materials it provides little advantage as a direct chlorination process for the production of specific ring-chlorinated products.

A more specific process for the ring-chlorination of p-xylene, utilizing acetic acid as a solvent and carried out in the presence of catalytic amounts of ferric chloride or iodine is disclosed in U.S. Pat. No. 3,002,027. The process limits the ring-chlorination to the formation of mono- and dichlorination derivatives. The 2,5-dichloro-p-xylene isomer may be separated from the crude reaction product by pouring into water followed by re-crystallization of the precipitate from a suitable solvent such as an organic alcohol or acetic acid.

It is further known from U.S. Pat. No. 3,035,103, that p-xylene may be chlorinated, in a solvent, such as carbon tetrachloride, in the presence of a catalyst such as ferric chloride to yield a mixture of mono-, di-, tri-, and tetra- ring-chlorinated p-xylenes which may then be distilled and the dichloro-para-xylene fraction treated with a lower alkanol to recover the commercially desirable 2,5-dichloro-p-xylene.

Although the processes of the prior art are useful in the preparation of chlorinated xylenes and, with subsequent separation, the isolation of 2,5-dichloro-p-xylene, it will be appreciated that further improvements in the efficiency, economy of preparation and yield of the desired product, 2,5-dichloro-p-xylene, are nevertheless desirable.

In addition, it is known from U.S. Pat. No. 3,226,447 to Bing et al, that the ring chlorination of toluene, benzene, or chlorinated benzene may be advantageously carried out in the presence of a catalyst comprising a halide of iron, aluminum or antimony and a co-catalyst consisting of an organic sulfur compound characterized by divalent sulfur, to provide a chlorinated product wherein the yield of para-chloro isomer is substantially increased. It is further disclosed by the patentee that such a catalyst system may be employed in the further chlorination of chlorobenzene to provide a product high in 1,2,4,5-tetrachlorobenzene. However, although the process disclosed is useful in the further chlorination of chlorobenzenes or in the chlorination of benzene or toluene where a high yield of para-chloro isomer is desired, no indication is seen of the effect of such a catalyst system on the chlorination of dialkyl benzenes such as p-xylene wherein the para position is filled with an alkyl group.

Accordingly, it is an object of the present invention to provide a simple, direct process for the preparation of 2,5-dichloro-p-xylene of high purity whereby the number of processing and handling steps is minimized. It is a further object to provide a process for the catalytic chlorination of p-xylene that maximizes the yield of 2,5-dichloro-p-xylene while minimizing the yield of the unwanted 2,3-dichloro-p-xylene and over- and underchlorinated products.

SUMMARY OF THE INVENTION

It has now been found that high yields of 2,5-dichloro-p-xylene are obtained when p-xylene is reacted with chlorine in the presence of a catalyst selected from the group consisting of halides of iron, halides of antimony, and mixtures thereof and a co-catalyst selected from the group consisting of organic sulfur compounds characterized by divalent sulfur. Halides of iron and/or antimony which may be employed in accordance with this invention include, for example, $FeCl_2$, $FeCl_3$, $FeBr_2$, $FeBr_3$, $SbCl_3$, $SbCl_5$, $SbOCl$, $SbBr_3$, and the like, as well as mixtures thereof. Divalent sulfur compounds which may be employed as co-catalysts in accordance with the present invention include, for example dialkyl sulfides, diaryl sulfides, alkylaryl sulfides, cyclic sulfides and the like, and mixtures thereof.

The chlorination process of this invention may be carried out in the presence of a suitable solvent, such as carbon tetrachloride, chloroform, polychloro and perchloroalkanes and the like which is inert to reaction with chlorine under conditions of the chlorination. However, it is an advantage of the process of the present invention, that it may be efficiently carried out in the absence of a solvent, thus eliminating the need for an additional separation step in the isolation of the desired product. The amount of catalyst system employed may vary considerably, for example from about 0.01 percent by weight or less to about 10.0 percent by weight or higher, based on the weight of p-xylene. Preferably, between about 0.1 and 1.0 percent by weight of catalyst system based on the weight of p-xylene, is employed. The proportion of catalyst to co-catalyst may vary considerably, but will typically be in the range of a molar ratio of catalyst:co-catalyst of from about 1:10 to 10:1 and preferably from about 1:4 to 1:1.

To maximize the yield of 2,5-dichloro-p-xylene as well as to minimize the formation of higher chlorinated products, it is advantageous to employ a nearly stoichiometric quantity of chlorine, for example about 1.8 to 2.1 moles of chlorine per mole of p-xylene although other ratios can be used.

The reaction temperature may vary considerably but is preferably in the range of about 0° to about 100° Celsius, and most preferably in the range of about 25° to about 70° Celsius. It has been found expedient to initiate the reaction at about room temperature, such as 25° Celsius and gradually increase the reaction temperature to about 50° to 70° Celsius during the reaction. Although the process of this invention is preferably carried out at atmospheric pressure, sub-atmospheric or super-atmospheric pressures may be employed, if desired. Upon completion of the reaction, any remaining by-product hydrogen chloride formed during the reaction, and any residual chlorine gas, may be conveniently removed, in a known manner, by blowing air or nitrogen through the mixture.

Typically, the crude chlorination product obtained in accordance with the process of this invention contains, after removal of HCl, about 0 to 6 percent by weight of 2-chloro-p-xylene, about 65 to 80 percent by weight of 2,5-dichloro-p-xylene, about 3 to 20 percent by weight of 2,3-dichloro-p-xylene, about 0 to 8 percent by weight 2,3,5-trichloro-p-xylene and trace amounts, generally less than one percent of 2,3,5,6-tetrachloro-p-xylene. This crude product is readily susceptible to simple purification steps to yield a 2,5-dichloro-p-xylene product having a purity in excess of about 90 percent.

If the reaction is run in a solvent may be conveniently removed in a known manner, for example, by distillation. Alternately, the 2,5-dichloro-p-xylene may be obtained directly by filtration of the reaction mixture. If the reaction is run in the absence of a solvent, the solvent separation step is omitted. The crude reaction product may then be treated by crystallization from suitable solvent in which the 2,5-dichloro-p-xylene is substantially insoluble while the major portion of the remaining chlorinated products is soluble. Solvents suitable for this purpose include for example, alkanols, especially the lower alkanols such as methanol, ethanol, n-propanol, isopropanol and the various isomeric butanols. The preferred solvent for this purpose is isopropanol. Generally the amount of alkanol will range from about 0.25 parts to about 10.0 parts by weight and preferably from about 0.5 to about 5.0 parts by weight of solvent per part of crude reaction product. The solid portion of the resulting mixture is then filtered, preferably at about room temperature (such as 25° Celsius) and dried. The resulting solid will, typically, exhibit a melting point in the range of 64.5° to 66.5° Celsius which corresponds closely to that of 2,5-dichloro-p-xylene of high purity. Gas chromatographic analysis of the product thus obtained typically discloses a composition of approximately 94 percent 2,5-dichloro-p-xylene, approximately 4 percent of 2,3-dichloro-p-xylene and approximately 2 percent of 2,3,5-trichloro-p-xylene.

The following specific examples will serve to further illustrate the present invention and manner in which it may be practiced. It will be understood, however, that such examples are illustrative of the way in which the invention may be carried out and are not to be construed as limitative thereof. In the examples, as well as elsewhere in the specification and claims appended thereto, parts and percentages are by weight and temperatures are in degrees Celsius unless otherwise stated.

EXAMPLE I

A mixture of approximately 106 parts of p-xylene, 0.42 parts of dioctyl sulfide and 0.21 parts of antimony trichloride was charged to a reaction vessel at an initial temperature of about 25° C. Chlorine (136 parts) was introduced into the reaction mixture over about four hours. During the initial stage of the chlorination reaction the temperature of the reaction mixture was gradually raised to about 65° C and maintained thereat for the remainder of the reaction period. Following the chlorination reaction, the reaction mixture was purged with nitrogen to remove hydrogen chloride and any residual chlorine. The crude product was analyzed by gas chromatographic methods with the following results:

| | |
|---|---|
| 2,5-dichloro-p-xylene | 78.4 percent |
| 2,3-dichloro-p-xylene | 12.5 percent |
| trichloro-p-xylene | 9.1 percent |

When the crude product is mixed with isopropanol, preferably at a temperature such that the product is in liquid phase, such as about 60° to 70° C and the mixture cooled to about 25°, the product obtained by crystallization from the mixture is 2,5-dichloro-p-xylene having a purity of greater than 90 percent.

EXAMPLE II

A mixture of about 106 parts of xylene, 0.42 parts of bis (p-chlorophenyl) sulfide and 0.21 parts of antimony trichloride was charged to a reaction vessel at an initial temperature of about 25° C and chlorine was introduced into the reaction mixture. The temperature of the reaction mixture was increased gradually to about 67° C during the initial stage of the chlorination reaction and maintained at approximately that temperature during the remainder of the reaction period. Over a total reaction period of approximately four hours a total of about 148 parts of chlorine was introduced into the reaction mixture. Following the chlorination reaction, the reaction mixture was purged with nitrogen to remove hydrogen chloride and any residual chlorine. The resulting crude product was analyzed by gas chromatographic methods with the following results:

| | |
|---|---|
| 2-chloro-p-xylene | 1.4 percent |
| 2,5-dichloro-p-xylene | 80.9 percent |
| 2,3-dichloro-p-xylene | 13.8 percent |
| trichloro-p-xylene | 3.9 percent |

Mixing of the crude product with isopropanol and crystallization therefrom yields 2,5-dichloro-p-xylene having a purity of greater than 90 percent.

EXAMPLE III

The procedure of Example II was repeated except that in place of 0.21 parts of antimony chloride, an equal amount of ferric chloride was employed; maximum reaction temperature was 70° C; and total of 152 parts of chlorine was introduced over a four hour period. The crude product was analyzed by gas chromatographic method with the following results:

| | | |
|---|---|---|
| 2-chloro-p-xylene | less than | 0.1 percent |
| 2,5-dichloro-p-xylene | | 78.0 percent |
| 2,3-dichloro-p-xylene | | 11.2 percent |
| trichloro-p-xylene | | 10.6 percent |

EXAMPLE IV

A mixture of 106.2 parts of p-xylene, 0.42 parts of bis (p-chlorophenyl) sulfide, 0.21 parts of antimony trichloride, in 100 parts of carbon tetrachloride was charged to a reaction vessel at an initial temperature of about 25° C and chlorine was introduced slowly into the reaction mixture. During the initial stage of the chlorination reaction the temperature was gradually increased to 55° C and maintained at approximately that temperature for the remainder of the reaction period. Over a reaction period of about nine hours, a total of about 159 parts of chlorine was introduced into the reaction mixture.

The reaction mixture was purged with nitrogen to remove hydrogen chloride and residual chlorine, and solvent removed by distillation. The resultant solid was analyzed by gas chromatographic methods with the following results:

| | |
|---|---|
| 2-chloro-p-xylene | 8.3 percent |
| 2,5-dichloro-p-xylene | 77.3 percent |
| 2,3-dichloro-p-xylene | 13.4 percent |
| trichloro-p-xylene | 0.5 percent |

EXAMPLE V

For purposes of comparison, ferric chloride, a known prior art catalyst, was employed as the sole catalyst component in the chlorination of p-xylene following a procedure similar to that of the previous examples. Thus, a mixture of 106.2 parts of p-xylene and 0.53 parts of ferric chloride was charged to a reaction vessel and heated to about 55° C. The reaction temperature was maintained at about 55° C to 60° C while 142 parts of chlorine was introduced slowly over a period of about 3 hours. The reaction product was purged with nitrogen to remove hydrogen chloride and any residual chlorine. The crude product was analyzed by gas chromatographic method with the following results:

| | |
|---|---|
| 2-chloro-p-xylene | 13.9 percent |
| 2,5-dichloro-p-xylene | 47.5 percent |
| 2,3-dichloro-p-xylene | 19.1 percent |
| trichloro-p-xylene | 17.6 percent |
| tetrachloro-p-xylene | 1.9 percent |

What is claimed is:

1. A process for the preparation of 2,5-dichloro-p-xylene comprising the steps of:
   A. reacting p-xylene with chlorine at a temperature of about 0° to about 100° Celsius in the presence of about 0.1 to about 1.0 percent by weight, based on the weight of p-xylene, of a catalyst system comprising a catalyst selected from the group consisting of $FeCl_2$, $FeCl_3$, $FeBr_3$, $SbCl_3$, $SbCl_5$, SbOCl and $SbBr_3$ and a co-catalyst selected from the group consisting of dialkyl sulfides, diaryl sulfides, alkylaryl sulfides and cyclic sulfides, said catalyst and co-catalyst being present in a molar proportion of catalyst: co-catalyst of about 1:4 to about 1:1, to form a crude 2,5-dichloro-p-xylene product; and
   B. mixing said crude product, in the liquid phase, with about 0.5 to about 5.0 parts by weight of isopropanol, per part of crude product, to remove by solution the soluble portions thereof; and
   C. recovering therefrom, as a solid, insoluble product, a purified 2,5-dichloro-p-xylene product.

2. A process for the preparation of 2,5-dichloro-p-xylene comprising the steps of:
   A. reacting p-xylene with chlorine at a temperature of about 0° to about 100° Celsius in the presence of about 0.1 to about 1.0 percent by weight, based on the weight of p-xylene, of a catalyst system comprising a catalyst selected from antimony chloride and ferric chloride, and a co-catalyst selected from bis(p-chlorophenyl) sulfide and dioctyl sulfide in a molar proportion of catalyst: co-catalyst of about 1:4 to about 1:1, to form a crude 2,5-dichloro-p-xylene product; and
   B. mixing said crude product, in the liquid phase, with about 0.5 to about 5.0 parts by weight of isopropanol, per cent of crude product to remove by solution the soluble portions thereof; and
   C. recovering by filtration therefrom, a purified 2,5-dichloro-p-xylene product.

3. A process according to claim 2 wherein said catalyst is antimony trichloride.

4. A process according to claim 3 wherein said co-catalyst is dioctyl sulfide.

5. A process according to claim 3 wherein said co-catalyst is bis(p-chlorophenyl) sulfide.

6. A process according to claim 2 wherein said catalyst is ferric chloride.

7. A process according to claim 6 wherein said co-catalyst is bis(p-chlorophenyl) sulfide.

* * * * *

UNITED STATES PATENT OFFICE
CERTIFICATE OF CORRECTION

PATENT NO. : 4,010,214
DATED : March 1, 1977
INVENTOR(S) : Samuel Gelfand

It is certified that error appears in the above-identified patent and that said Letters Patent are hereby corrected as shown below:

Column 3, line 15 , "If the reaction is run in a solvent may be conveniently" should read --If the reaction is run in a solvent, the solvent may be conveniently--. Column 6, line 31, "per cent of crude" should read --per part of crude--.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks